United States Patent [19]

Schwan et al.

[11] 3,932,452

[45] Jan. 13, 1976

[54] 1-ARYLMETHYL-2-IMIDAZOLIDINONES

[75] Inventors: Thomas J. Schwan; Nelson J. Miles, both of Norwich, N.Y.

[73] Assignee: Morton-Norwich Products, Inc., Norwich, N.Y.

[22] Filed: Feb. 7, 1975

[21] Appl. No.: 547,925

[52] U.S. Cl............ 260/309.7; 260/296 R; 424/263; 424/273
[51] Int. Cl.²......................................... C07D 49/34
[58] Field of Search................................. 260/309.7

[56] References Cited
UNITED STATES PATENTS

| | | | |
|---|---|---|---|
| 2,514,380 | 7/1950 | Duschinsky | 260/309.7 |
| 2,518,264 | 8/1950 | Abramovitch | 260/309.7 |
| 3,196,152 | 7/1965 | Wright, Sr. et al. | 260/309.7 X |
| 3,459,757 | 8/1969 | Wright, Jr. et al. | 260/309.7 X |
| 3,636,039 | 1/1972 | Gruenman et al. | 260/309.7 |

OTHER PUBLICATIONS

Chem. Abstracts, 57 : 9860b.

*Primary Examiner*—Ethel G. Love
*Attorney, Agent, or Firm*—Anthony J. Franze

[57] ABSTRACT

A series of 1-arylmethyl-2-imidazolidinones are useful as antidepressant agents.

12 Claims, No Drawings

1-ARYLMETHYL-2-IMIDAZOLIDINONES

This invention is concerned with chemical compounds. More particularly it deals with compounds of the formula:

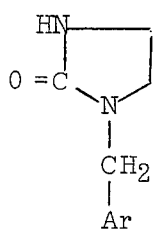

wherein Ar is selected from the group consisting of benzhydryl, 2-naphthyl, 5-bromo-2-naphthyl, 4-pyridyl, and

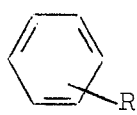

wherein R is 2-fluoro, 4-bromo, 2,6-dichloro, 2,4-dichloro, 2-hydroxy-5-nitro, 4benzyloxy, 3,4-difluoro or 4-cyano. These compounds possess pharmacologic properties. Particularly, these compounds affect the central nervous system. They exhibit anticonvulsant properties evidenced by the control of pentylenetetrazol induced convulsions in mice. Thus, an oral dose of from 50–200 mg/kg of these compounds to mice intravenously receiving 45 mg/kg of pentylenetrazol counteracts the convulsive property of that agent.

The compounds of this invention are currently prepared according to the following schema:

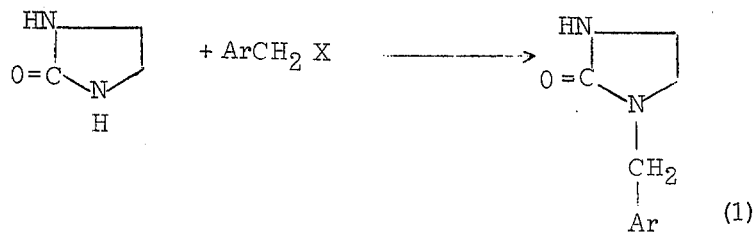

wherein X is halogen. Preferably this reaction is carried out in the presence of potassium carbonate and potassium iodide and an inert solvent such as dimethylsulfoxide or dimethylformamide.

This reaction is readily carried out in a solvent such as dioxane.

The following examples are illustrative of the preparation of the compounds of this invention according to the above schema.

EXAMPLE I

1-(Diphenylmethyl)-2-imidazolidinone

A 21.5 g (0.25 mole) portion of 2-imidazolidinone in 250 ml of dimethylsulfoxide was treated with 34.5 g (0.25 mole) of $K_2CO_3$, 20 g (0.12 mole) of KI and 50.8 g (0.25 mole) of benzhydryl chloride. The reaction mixture was heated with rapid stirring to 100° over 0.3 hr, held at 100° for 1.5 hours and poured into 1.5 l of $H_2O$. The aqueous mixture was extracted with 1.3 l of chloroform. The chloroform extract was washed with 500 ml of $H_2O$, dried over $MgSO_4$ overnight and filtered. The filtrate was concentrated to dryness under reduced pressure leaving 27 g (43%) of a semi-solid. The crude product was washed with 100 ml of ether, air dried and dried at 60° for 2 hours to give 19 g (30%) of a white solid, m.p. 200°–202°. Recrystallization from acetonitrile provided an analytical sample, m.p. 201°–203°.

Anal. Calcd. for $C_{16}H_{16}N_2O$: C, 76.16; H, 6.39; N, 11.10. Found: C, 75.91; H, 6.52; N, 11.32.

EXAMPLE II

1-(2-Naphthylmethyl)-2-imidazolidinone

A 21.5g (0.25 mole) portion of 2-imidazolidinone in 250 ml of dimethylsulfoxide was treated with 34.5 g (0.25 mole) of $K_2CO_3$, 20 g (0.12 mole) of KI and 44.3 g (0.25 mole) of 2-(chloromethyl)-naphthalene. The reaction mixture was heated to 105° over 0.3 hours, held at 105°–110° for 1.8 hours and poured with rapid stirring into 1.5 l of water. The aqueous mixture was extracted with 1.3 l of chloroform. The chloroform extract was washed with 500 ml of water, dried over

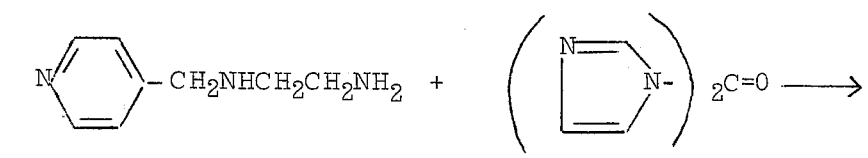

MgSO₄ overnight and filtered. The filtrate was concentrated to dryness to give 31.5 g (56%) of a light yellow solid, m.p. 102 soften, 120°–138°.

The crude product was recrystallized from 400 ml of acetonitrile, washed with 200 ml of ether, air dried, and dried 2 hours at 60°, m.p. 133°–144°. Yield: 23 g. (41%)

A 22 g portion of the above recrystallized product was recrystallized from 825 ml of methanol, cooled to room temperature, stored for 4 hours at room temperature, and filtered. The white pearlescent solid (6.0 g, 1,3-disubstituted product) was saved, m.p. 167°–170°. The filtrate was concentrated to a volume of 75 ml, cooled and filtered. The white solid was washed with 50 ml of methanol, then ether, and air dried, m.p. 149°–152°. Yield: 11.5 (50%). Recrystallization from methanol provided an analytical sample, m.p. 148°–151°.

Anal. Calcd. for $C_{14}H_{14}N_2O$: C, 74.31; H, 6.24; N, 12.38. Found: C, 74.57; H, 6.27; N, 12.03.

EXAMPLE III

1-[(5-Bromo-2-naphthyl)methyl]-2-imidazolidinone

A. 5-Bromo-2-Naphthoic Acid

A 75 g (0.44 mole) portion of 2-naphthoic acid, 375 ml of acetic acid, 22.5 ml of $Br_2$(70 g, 0.44 mole) and 1.9 g (0.015 mole) of $I_2$ were placed in a 1 l. 3-necked flask and refluxed with stirring for 0.6 hours. The reaction mixture was cooled to 25° and filtered. The cream solid was washed with small portions of the filtrate, air dried and dried to a constant weight at 60° to give 76 g (75%) of a light tan-cream solid, m.p. 224°–233° dec.

The crude product was slurried with 375 ml of 1 N NaOH for 0.5 hours and filtered. The cream colored sodium salt was washed with portions of the filtrate and air dried. The damp cake was taken up in 300 ml of $H_2O$, acidified with 50 ml of HCl, stirred for 4 hours, filtered, washed with 100 ml of $H_2O$, air dried, and dried to a constant weight at 60°, m.p. 257°–259° dec. Yield: 42 g (42%)

B. 2-Bromo-5-(hydroxymethyl)-naphthalene

A 42 g (0.167 mole) portion of 5-bromo-2-naphthoic acid in 460 ml of toluene was treated with 460 ml (0.58 mole) of diisobutylaluminum hydride over 0.4 hours at 20°–25° with rapid stirring. The reaction mixture was then allowed to stand for 1 hour at ambient temperature, heated slowly to reflux over 0.5 hours, refluxed for 0.5 hours, allowed to cool slowly to room temperature and allowed to stand overnight at room temperature with stirring. The reaction mixture was then treated at 25°–30° with 36 ml of 1:1 $H_2O$-methanol, 18 ml of concentrated HCl and 200 ml of $H_2O$. The organic layer was separated, dried over MgSO₄, filtered and concentrated under reduced pressure to give 39.5 g (97%) of a light yellow oil which crystallized, m.p. 72°–75°.

Further extraction of the aqueous phase with 300 ml of toluene gave an additional 1.0 g (3%) of the desired product, m.p. 71°–75°.

C. 2-Bromo-5-(chloromethyl)-naphthalene

A 39.5 g (0.167 mole) portion of 2-bromo-5-(hydroxymethyl)-naphthalene in 300 ml of chloroform was treated at 0°–5° over 0.3 hours with 75 ml (123 g, 1.03 mole) of $SOCl_2$. The reaction mixture was allowed to warm to room temperature over 0.5 hours, heated to reflux over 0.2 hours, and allowed to cool slowly to room temperature and filtered. The filtrate was concentrated under reduced pressure. The residue was taken up in 150 ml of benzene and again concentrated under reduced pressure to give 43 g (100%) of a light yellow oil which crystallized, m.p. 73°–76°.

D. 1-[(5-Bromo-2-naphthyl)methyl]-2-imidazolidinone

An 18.9 g (0.22 mole) portion of 2-imidazolidinone, 23.8 g (0.17 mole) of $K_2CO_3$, 16.4 g (0.099 mole) of KI, 44 g (0.17 mole) of 2-bromo-5-(chloromethyl)-naphthalene in 397 ml of dimethylsulfoxide was heated rapidly with stirring to 105° over 0.3 hours and held at 105°–110° for 1.7 hours. The hot reaction mixture was poured into 550 ml of $H_2O$ and stirred for 0.1 hours. The hydrolysis mixture was extracted with three 330 ml portions of chloroform. The chloroform extracts were combined, washed with 220 ml of $H_2O$, dried over MgSO₄ and filtered. The filtrate was concentrated under reduced pressure to give 32 g (62%) of light yellow oil.

The crude product was then repeatedly washed with a total of four 200 ml portions of heptane to give 30 g of a light yellow oil. The crude oil was extracted with 800 ml of an $H_2O$-methanol solution (1 part by volume of $H_2O$ to 9 parts by volume of methanol). The extract was allowed to cool to room temperature and filtered. The filtrate was concentrated hard under reduced pressure to give 10 g (19%) of a pale yellow oil. The oil was crystallized using 60 ml of acetone to give the desired product, a white solid, m.p. 161°–163°. Yield: 2.3 g (4.3%).

The filtrate was then concentrated under reduced pressure to give 6 g of a light yellow oil which was crystallized with 30 ml of ether to give an additional 0.5 g (1%) of the desired product, m.p. 158°–161°. Recrystallization from acetone gave an analytical sample, m.p. 162°–163°.

Anal. Calc'd. for $C_{14}H_{13}BrN_2O$: C, 55.10; H, 4.29; N, 9.18. Found: C, 55.53; H, 4.44; N, 9.00.

EXAMPLE IV 1-(2-Fluorobenzyl)-2-imidazolidinone

A 21.5 g (0.25 mole) portion of 2-imidazolidinone in 125 ml of dimethylsulfoxide was treated with 34.5 g (0.25 mole) of $K_2CO_3$, 20 g (0.12 mole) of KI and 36.3 g (0.25 mole) of 2-fluorobenzyl chloride. The reaction mixture was heated to 105° over 0.3 hours, held at 105° for 1.8 hours, and poured into 1.5 l of water all with rapid stirring. The aqueous mixture was extracted with 1.3 l of chloroform. The chloroform extract was washed with 500 ml of $H_2O$, dried over MgSO₄ overnight and filtered. The filtrate was concentrated under reduced pressure to give 42 g (86%) of a light yellow oil. The crude product was washed with 100 ml of ether to give 10 g (20%) of a white solid m.p. 72°–76°.

The crude product was recrystallized from 12 ml of benzene, washed with ether and air dried m.p. 74°–77°. Yield: 7.5 g (15%). Recrystallization from acetonitrile gave an analytical sample, m.p. 76°–79°.

Anal. Calcd. for $C_{10}H_{11}FN_2O$: C, 61.84; H, 5.71; N, 14.43. Found: C, 61.61; H, 5.72; N, 14.38.

EXAMPLE V 1-(4-Bromobenzyl)-2-imidazolidinone

A 12.4 g (0.14 mole) portion of 2-imidazolidinone in 125 ml of dimethylsulfoxide treated with 19.9 g (0.14 mole) of $K_2CO_3$, 11.5 g (0.069 mole) of KI and 36.0 g (0.14 mole) of 4-bromobenzylbromide. The reaction mixture was heated to 105° over 0.3 hours, held at 105° with stirring for 1.8 hours, and poured into 1.5 l of cold water. The aqueous mixture was extracted with 1.3 l of chloroform. The chloroform extract was washed with 500 ml of water, dried over $MgSO_4$ overnight and filtered. The filtrate was concentrated under reduced pressure to give 36 g (100%) of a light yellow semi-solid. The crude product was crystallized using 150 ml of ether, filtered, air dried and dried at 60° for 4 hours to give 15 (42%) of a white solid m.p. 163°–167°. Recrystallization from acetonitrile gave an analytical sample, m.p. 166°–168°.

Anal. Calc'd. for $C_{10}H_{11}BrN_2O$: C, 47.08; H, 4.35; N, 10.98. Found: C, 47.10; H, 4.28; N, 10.98.

EXAMPLE VI

1-(2,6-Dichlorobenzyl)-2-imidazolidinone

A 21.5 g (0.25 mole) portion of 2-imidazolidinone in 250 ml of dimethylsulfoxide was treated with 34.5 g (0.25 mole) of $K_2CO_3$, 20 g (0.12 mole) of KI and 48.9 g (0.25 mole) of 2,6-dichlorobenzyl chloride. The reaction mixture was heated to 105° over 0.3 hours, held at 105° for 1.7 hours and poured into 1.5 l of water all with rapid stirring. The aqueous mixture was extracted with 1.3 l of chloroform. The chloroform extract was washed with 500 ml of water, dried over $MgSO_4$ overnight and filtered. The filtrate was concentrated under reduced pressure leaving 48 g (79%) of a light yellow viscous oil. The crude product was crystallized using 125 ml of ether, filtered, air dried and dried to a constant weight at 60° to give 13 g (21%) of a white solid m.p. 156°–158°.

Anal. Calc'd. for $C_{10}H_{10}Cl_2N_2O$: C, 49.00; H, 4.11; N, 11.43. Found: C, 49.01; H, 3.95; N, 11.38.

EXAMPLE VII

1-(2,4-Dichlorobenzyl)-2-imidazolidinone

A 21.5 g (0.25 mole) portion of 2-imidazolidinone in 200 ml of dimethylsulfoxide was treated with 34.5 g (0.25 mole) of $K_2CO_3$, 20 g (0.12 mole) of KI and 48.9 g (0.25 mole) of 2,4-dichlorobenzyl chloride. The reaction mixture was heated with stirring to 105° over 0.3 hours, held at 105° for 1.8 hours, and poured with rapid stirring into 1.5 l of water. The aqueous mixture was extracted with 1.3 l of chloroform. The chloroform extract was washed with 580 ml of water, dried over $MgSO_4$ overnight and filtered. The filtrate was concentrated under reduced pressure leaving 47 g (77%) of a light yellow oil. The oil was crystallized with 125 ml of ether, filtered, air dried, and dried to a constant weight at 60° to give 19 g (31%) of a white solid, m.p. 116°–118°.

Anal. Calc'd. for $C_{10}H_{10}Cl_2N_2O$: C, 49.00; H, 4.11; N, 11.43. Found: C, 48,93; H, 4.23; N, 11.82.

EXAMPLE VIII

1-(2-Hydroxy-5-nitrobenzyl)-2-imidazolidinone

A 7.9 g (0.092 mole) portion of 2-imidazolidinone in 92 ml of dimethylsulfoxide was treated with 12.7 g (0.092 mole) of $K_2CO_3$, 7.4 g (0.045 mole) of potassium iodide and 20.0 g (0.092 mole) of 2-hydroxy-5-nitrobenzyl bromide. The reaction mixture was heated to 105° over 0.3 hours and held at 105° for 1.6 hours. The reaction mixture was poured with stirring into 550 ml of water. The aqueous mixture was acidified with 9 ml of concentrated HCl and extracted with 480 ml of chloroform. The chloroform extract was washed with 60 ml of $H_2O$, dried over $MgSO_4$ overnight and filtered. The filtrate was concentrated under reduced pressure to give 18 g of a yellow semi-solid. The crude product was crystallized using 65 ml of benzene and filtered, washing with ether to give 9.7 g (44%) of a light yellow semi-solid. Recrystallization from acetonitrile gave an analytical sample, m.p. 222°–224° dec.

Anal. Calc'd. for $C_{10}H_{11}N_3O_4$: C, 50.63; H, 4.67; N, 17.72. Found: C, 50.77; H, 4.73; N, 17.45.

EXAMPLE IX

1-(4-Benzyloxybenzyl)-2-imidazolidinone

A 21.5 g (0.25 mole) portion of 2-imidazolidinone in 250 ml of dimethylsulfoxide was treated with 34.5 (0.25 mole) of $K_2CO_3$, 20.0 g (0.12 mole) of KI and 58.5 g (0.25 mole) of 4-benzyloxybenzyl chloride. The reaction mixture was heated to 105° over 0.5 hours, held at 105°–110° for 1.7 hours, poured with stirring into 1.5 l of $H_2O$, stirred for 0.3 hours and filtered. The green-yellow solid was washed with 300 ml of $H_2O$, air dried overnight, and dried to a constant weight at 60°, m.p. 110°–122°. Yield: 62 g (87%). Recrystallization from 1:1 methane: water gave an analytical sample, m.p. 156°–157°.

Anal. Calc'd. for $C_{17}H_{18}N_2O_2$: C, 72.32; H, 6.43; N, 9.92. Found: C, 72.57; H, 6.47; N, 9.78.

EXAMPLE X

1-(3,4-Difluorobenzyl)-2-imidazolidinone

To a 17.6 g (0.205 mole) portion of 2-imidazolidinone in 150 ml of dimethylsulfoxide was added 28.4 g (0.205 mole) of $K_2CO_3$, 17.0 g (0.096 mole) of KI and 33.2 g (0.204 mole) of 3,4-difluorobenzyl chloride. The reaction mixture was heated, with stirring, to 105° over 0.5 hours, held at 105° for 1.7 hours and poured with stirring into 250 ml of water. The aqueous mixture was extracted with two 250 ml portions of chloroform. The chloroform extracts were washed with 100 ml of $H_2O$, dried over $MgSO_4$ and filtered. The filtrate was concentrated under reduced pressure to give 42 g (96%) of a light yellow semi-solid which was washed with 50 ml of heptane and crystallized using 30 ml of ether. The white solid was collected, washed with 20 ml of ether, air dried, and dried to a constant weight at 60°, m.p. 112°–114°. Yield: 4.4 g (10%).

The heptane washing was combined with the above filtrate, concentrated under reduced pressure and stored in an open petri dish in the hood for 1 week. The residue, a semi-solid, was taken up in 30 ml of ether, cooled and filtered. The white solid was washed with 15 ml of ether, air dried, and dried to a constant weight at 60°, m.p. 112°–114°. Yield: 6.6 g (15%). Recrystallization from acetonitrile gave an analytical sample, m.p. 112°–113°.

Anal. Calc'd. for $C_{10}H_{10}F_2N_2O$: C, 56.60; H, 4.75; N, 13.20. Found: C, 56.80; H, 4.73; N, 13.19.

EXAMPLE XI

1-(4-Cyanobenzyl)-2-imidazolidinone

A mixture of 20.95 g (0.107 mole) of 4-cyanobenzyl bromide, 14.7 g (0.107 mole) $K_2CO_3$, 5.0 g KI, and 10.32 g (0.12 mole) 2-imidazolidinone in 125 ml dimethylsulfoxide was stirred at 100°–110° for 30 minutes, cooled, and poured into 400 ml cold tap water.

The mixture was stirred at room temperature for 30 minutes and extracted with 250 ml chloroform. The chloroform extract was washed with 3 × 250 ml H₂O, dried (MgSO₄), and concentrated to dryness in vacuo to give an oily residue. Crystallization from 60 ml toluene gave 5.50 g of the crude product. Further recrystallization from toluene gave 4.34 g (20%) of the nitrile, m.p. 127°–133°. The analytical sample, m.p. 134°–136°, was obtained by recrystallization from toluene.

Anal. Calc'd. for $C_{11}H_{11}N_3O$: C, 65.67; H, 5.51; N, 20.88. Found: C, 65.75; H, 5.55; N, 20.72.

EXAMPLE XII 1-(4-Picolyl)-2-imidazolidinone

A 20.0 g (0.13 mole) portion of N-(4-picolyl)ethylenediamine in 170 ml of dry dioxane was treated with 23.8 g (0.15 mole) of 1,1′carbonyldiimidazole (98%) over 0.1 hours with a temperature rise to 50°. The reaction mixture was stirred for 2.5 hours at room temperature, with crystallization at 1 hour, stored overnight at room temperature, refluxed for 4 hours, cooled to 5°–10° for 0.5 hours and filtered.

The white solid was washed with one-half of the filtrate, 25 ml of ether and air dried, m.p. 150°–153°. Yield: 15.5 g (67%).

The initial product was recrystallized from 105 ml of acetonitrile, washed with one-half of the filtrate, ether and air dried to give 10.5 g (46%) of the desired product, m.p. 153°–155°. Recrystallization from acetonitrile gave an analytical sample, m.p. 151°–153°.

Anal. Calc'd. for $C_9H_{11}N_3O$: C, 61.00; H, 6.20; N, 23.72. Found: C, 61.29; H, 6.15; N, 23.88.

What is claimed:

1. A compound of the formula:

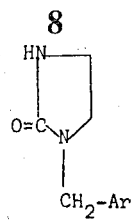

wherein Ar is selected from the group consisting of benzhydryl, 2-naphthyl, 5-bromo-2-naphthyl,[4-pyridyl]and

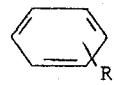

wherein R is 2-fluoro, 4-bromo, 2,6-dichloro, 2,4-dichloro, 2-hydroxy-5-nitro, 4-benzyloxy, 3,4-difluoro or 4-cyano.

2. The compound 1-(diphenylmethyl)-2-imidazolidinone.

3. The compound 1-(2-naphthylmethyl)-2-imidazolidinone.

4. The compound 1[(5-bromo-2-naphthyl)methyl]-2-imidazolidinone.

5. The compound 1-(2-fluorobenzyl)-2-imidazolidinone.

6. The compound 1-(4-bromobenzyl)-2-imidazolidinone.

7. The compound 1-(2,6-dichlorobenzyl)-2-imidazolidinone.

8. The compound 1-(2,4-dichlorobenzyl)-2-imidazolidinone.

9. The compound 1-(2-hydroxy-5-nitrobenzyl)-2-imidazolidinone.

10. The compound 1-(4-benzyloxybenzyl)-2-imidazolidinone.

11. The compound 1-(3,4-difluorobenzyl)-2-imidazolidinone.

12. The compound 1-(4-cyanobenzyl)-2-imidazolidinone.

* * * * *